(12) United States Patent
Wambaugh

(10) Patent No.: US 7,713,498 B2
(45) Date of Patent: May 11, 2010

(54) MANUFACTURING PLANT FOR THE DEHYDROGENATION OF AN UNSATURATED HYDROCARBON

(75) Inventor: James Allen Wambaugh, Amsterdam (NL)

(73) Assignee: Shell Oil Company, Houston, TX (US)

( * ) Notice: Subject to any disclaimer, the term of this patent is extended or adjusted under 35 U.S.C. 154(b) by 330 days.

(21) Appl. No.: 11/739,765

(22) Filed: Apr. 25, 2007

(65) Prior Publication Data
US 2008/0069745 A1 Mar. 20, 2008

Related U.S. Application Data

(62) Division of application No. 10/438,994, filed on May 15, 2003, now Pat. No. 7,244,868.

(51) Int. Cl.
*B01J 8/04* (2006.01)
*B01J 19/00* (2006.01)
*C07C 5/00* (2006.01)

(52) U.S. Cl. ............ 422/190; 422/192; 422/131; 585/441; 585/444; 585/445; 585/659

(58) Field of Classification Search ............ 422/192, 422/190, 131; 585/441, 659, 444, 445
See application file for complete search history.

(56) References Cited

U.S. PATENT DOCUMENTS

| 1,368,748 | A | | 2/1921 | Penniman, Jr. et al. | |
|---|---|---|---|---|---|
| 3,223,743 | A | | 12/1965 | MacFarlane | 260/669 |
| 3,686,346 | A | * | 8/1972 | Pitzer | 585/623 |
| 3,703,593 | A | | 11/1972 | Turley et al. | 252/470 |
| 3,904,552 | A | | 9/1975 | O'Hara | 252/458 |
| 4,144,197 | A | * | 3/1979 | Riesser | 502/304 |
| 4,389,517 | A | | 6/1983 | Priddy et al. | 526/64 |
| 4,720,604 | A | | 1/1988 | Chu | 585/445 |
| 4,758,543 | A | | 7/1988 | Sherrod et al. | 502/174 |
| 4,804,799 | A | | 2/1989 | Lewis et al. | 585/444 |
| 4,822,936 | A | | 4/1989 | Maurer et al. | 585/259 |
| 5,156,816 | A | | 10/1992 | Butler et al. | 422/141 |

(Continued)

FOREIGN PATENT DOCUMENTS

EP 0502510 12/1995

(Continued)

OTHER PUBLICATIONS

H. F. Marks, et al. (ED.), "Encyclopedia of Polymer Science and Engineering," 2nd Edition, New York, vol. 16, pp. 1-246, Mar. 20, 1989.

*Primary Examiner*—Walter D Griffin
*Assistant Examiner*—Natasha Young

(57) ABSTRACT

A manufacturing plant for carrying out a process for the catalytic dehydrogenation of a first unsaturated hydrocarbon to form a second unsaturated hydrocarbon which has one olefinically unsaturated bond more than the first unsaturated hydrocarbon and otherwise an unchanged carbon skeleton, which process comprises:
  contacting in a first step a feed comprising the first unsaturated hydrocarbon with a first dehydrogenation catalyst having a temperature parameter $T_1$ and a selectivity parameter $S_1$, and
  contacting in a second step a reaction product of the first step comprising the first unsaturated hydrocarbon and the second unsaturated hydrocarbon with a second dehydrogenation catalyst having a temperature parameter $T_2$ and a selectivity parameter $S_2$, such that $T_1<T_2$ and $S_1<S_2$.

10 Claims, 2 Drawing Sheets

U.S. PATENT DOCUMENTS

| | | |
|---|---|---|
| 5,171,914 A | 12/1992 | Hamilton, Jr. ............... 585/444 |
| 5,190,906 A | 3/1993 | Murakami et al. .......... 502/304 |
| 5,255,742 A | 10/1993 | Mikus ........................ 166/303 |
| 5,376,613 A | 12/1994 | Dellinger et al. ............ 502/304 |
| 5,401,485 A | 3/1995 | Hamilton, Jr. ............... 423/632 |
| 5,504,268 A | 4/1996 | van der Aalst et al. ...... 585/259 |
| 5,510,552 A | 4/1996 | Dellinger et al. ............ 585/444 |
| 5,597,547 A | 1/1997 | Hamilton, Jr. ............... 423/632 |
| 5,668,075 A | 9/1997 | Milam et al. ................ 502/338 |
| 5,689,023 A | 11/1997 | Hamilton, Jr. ............... 585/444 |
| 5,817,901 A | 10/1998 | Trambouze et al. ......... 585/259 |
| 5,911,967 A | 6/1999 | Ruthner ...................... 423/632 |
| 6,191,065 B1 | 2/2001 | Williams et al. ............ 502/300 |
| 6,465,704 B2 * | 10/2002 | Williams et al. ............ 585/444 |
| 6,623,707 B1 * | 9/2003 | Addiego et al. ............. 422/190 |
| 2002/0013429 A1 * | 1/2002 | Smit et al. .................... 526/65 |
| 2002/0065443 A1 | 5/2002 | Williams et al. ............ 585/444 |

FOREIGN PATENT DOCUMENTS

| | | |
|---|---|---|
| EP | 1027928 | 2/2000 |
| JP | 60193933 A | 10/1985 |
| JP | 4364135 A | 12/1992 |
| WO | WO9918392 | 4/1999 |

* cited by examiner

MANUFACTURING PLANT FOR THE DEHYDROGENATION OF AN UNSATURATED HYDROCARBON

This application is a divisional of prior application Ser. No. 10/438,994, filed May 15, 2003 now U.S. Pat. No. 7,244,868, which is hereby incorporated by reference.

FIELD OF THE INVENTION

The present invention relates to a process for the catalytic dehydrogenation of a first unsaturated hydrocarbon to form a second unsaturated hydrocarbon which has one olefinically unsaturated bond more than the first unsaturated hydrocarbon. The present invention also relates to a manufacturing plant which is suitable for carrying out the process of this invention.

BACKGROUND OF THE INVENTION

Processes for the catalytic dehydrogenation of an unsaturated hydrocarbon (hereinafter "first unsaturated hydrocarbon") to form an unsaturated hydrocarbon which has one olefinically unsaturated bond more than the first unsaturated hydrocarbon and otherwise an unchanged carbon skeleton, (hereinafter "second unsaturated hydrocarbon") are well known in the art. An example of such a dehydrogenation is the dehydrogenation of an alkylaromatic compound to yield, as the desired, main product, the corresponding alkenylaromatic compound. Another example is the dehydrogenation of a mono-olefin to yield as the desired, main product a corresponding conjugated di-olefin. The dehydrogenation catalysts customarily used in such processes are iron oxide based catalysts.

In such processes the dehydrogenation does not occur without side reactions, which decreases the yield of the desired second unsaturated hydrocarbon and therefore changes the economy of the process unfavourably.

For example, in the dehydrogenation of an alkylaromatic compound, one such side reaction is the formation of coke on the catalyst, of which in additional effect is that it decreases the catalyst lifetime. Other side reactions involve the formation of an alkynyl-aromatic compound, a methylaromatic compound, and a de-alkylated aromatic compound. For example, in the dehydrogenation of ethylbenzene, the desired, main product is styrene and undesired byproducts are coke, phenylacetylene, toluene and benzene.

In view of the applicability and use of the alkenylaromatic compound, the alkynylaromatic compound is frequently at least partly removed from the product of the dehydrogenation. This removal requires a separate process step, typically involving hydrogenation to the alkenylaromatic compound, using a selective hydrogenation catalyst.

Analogous side reactions may occur in the dehydrogenation of a mono-olefin.

In the past, much work has been carried out with the object of improving the activity and the selectivity of dehydrogenation catalysts, and the efforts are still going on. However, so far it has proved to be very difficult to improve the activity of a dehydrogenation catalyst without compromising the selectivity and to improve the selectivity without compromising the activity. Thus, the work has led to the development of so-called high activity dehydrogenation catalyst and so-called high selectivity dehydrogenation catalysts.

Compared with high selectivity dehydrogenation catalysts, high activity dehydrogenation catalysts may be operated advantageously at a relatively low temperature. Alternatively, they may be operated at relatively high space velocity, saving reactor volume and catalyst inventory for a certain reactor throughput. However, these advantages are at the cost of selectivity. Compared with high activity dehydrogenation catalysts, high selectivity dehydrogenation catalysts offer a relatively high selectivity, but they are operated at a relatively high temperature or at a relatively low space velocity.

U.S. Pat. No. 3,223,743 discloses a dehydrogenation process wherein the dehydrogenation feed is contacted first with a high selectivity dehydrogenation catalyst and subsequently with a high activity dehydrogenation catalyst, with the object of improving the conversion and yield of the desired dehydrogenation product. The teaching of U.S. Pat. No. 3,223,743 has found worldwide application in commercial dehydrogenation units. U.S. Pat. No. 3,223,743 is incorporated herein by reference.

As used in this patent document, the term "conversion" means in a quantitative sense the fraction, in % mole, of the first unsaturated hydrocarbon which is converted. The term "selectivity" means herein the fraction, in % mole, of converted first unsaturated hydrocarbon which yields the second unsaturated hydrocarbon.

The performance of dehydrogenation catalysts may be measured by catalyst testing methods. As used herein, the term "temperature parameter" means the test temperature, in ° C., at which the catalyst provides under isothermal testing conditions a conversion of 70% mole, and the term "selectivity parameter" means the selectivity then achieved. It is noted that, as the temperature parameter is a temperature at which a certain conversion (viz. 70% mole) is achieved, the temperature parameter is lower as the activity of a catalyst is higher.

High activity dehydrogenation catalysts have a relatively low temperature parameter and relatively low selectivity parameter. High selectivity dehydrogenation catalysts have a relatively high temperature parameter and relatively high selectivity parameter.

SUMMARY OF THE INVENTION

It has now surprisingly been found that in a particular configuration of different types of dehydrogenation catalysts a relatively high overall selectivity is achieved in the dehydrogenation process, whilst there is in addition an advantage in terms of a low operating temperature and/or a high space velocity. In this particular configuration the dehydrogenation feed is contacted with a high activity dehydrogenation catalyst and subsequently with a high selectivity dehydrogenation catalyst. This finding is unexpected, in particular in view of the teaching of U.S. Pat. No. 3,223,743.

Accordingly, the present invention provides a process for the catalytic dehydrogenation of a first unsaturated hydrocarbon to form a second unsaturated hydrocarbon which has one olefinically unsaturated bond more than the first unsaturated hydrocarbon and otherwise an unchanged carbon skeleton, which process comprises:

contacting in a first step a feed comprising the first unsaturated hydrocarbon with a first dehydrogenation catalyst having a temperature parameter $T_1$ and a selectivity parameter $S_1$, and contacting in a second step a reaction product of the first step comprising the first unsaturated hydrocarbon and the second unsaturated hydrocarbon with a second dehydrogenation catalyst having a temperature parameter $T_2$ and a selectivity parameter $S_2$, such that $T_1<T_2$ and $S_1<S_2$.

As used herein, "temperature parameter" means the temperature, in ° C., at which the dehydrogenation catalyst in question provides under defined testing conditions a conversion of the first unsaturated hydrocarbon of 70% mole, and "selectivity parameter" means the selectivity, in % mole, to the second unsaturated hydrocarbon which is then achieved. For the avoidance of doubt, when temperature parameters and selectivity parameters of different dehydrogenation catalysts are compared, such as by the expressions "$T_1<T_2$" and "$S_1<S_2$", they are deemed to have been measured under the same testing conditions.

The present invention also provides a manufacturing plant which is suitable for carrying out a process for the catalytic dehydrogenation of a first unsaturated hydrocarbon to form a second unsaturated hydrocarbon which has one olefinically unsaturated bond more than the first unsaturated hydrocarbon and otherwise an unchanged carbon skeleton, which plant comprises:

a first catalyst bed which is configured to receive a feed comprising the first unsaturated hydrocarbon, and which first catalyst bed comprises a first dehydrogenation catalyst having a temperature parameter $T_1$ and a selectivity parameter $S_1$, and a second catalyst bed which is configured to receive a reaction product formed in the first catalyst bed comprising the first unsaturated hydrocarbon and the second unsaturated hydrocarbon, and which second catalyst bed comprises a second dehydrogenation catalyst having a temperature parameter $T_2$ and a selectivity parameter $S_2$, such that $T_1, <T_2$ and $S_1<S_2$.

The present invention further provides a method of using a second unsaturated hydrocarbon for making polymers or copolymers, comprising polymerising the second unsaturated hydrocarbon to form a polymer or copolymer comprising monomer units derived from the second unsaturated hydrocarbon, wherein the second unsaturated hydrocarbon has been prepared in a process for the dehydrogenation of a first unsaturated hydrocarbon according to this invention.

DETAILED DESCRIPTION OF THE INVENTION

Figure 1:
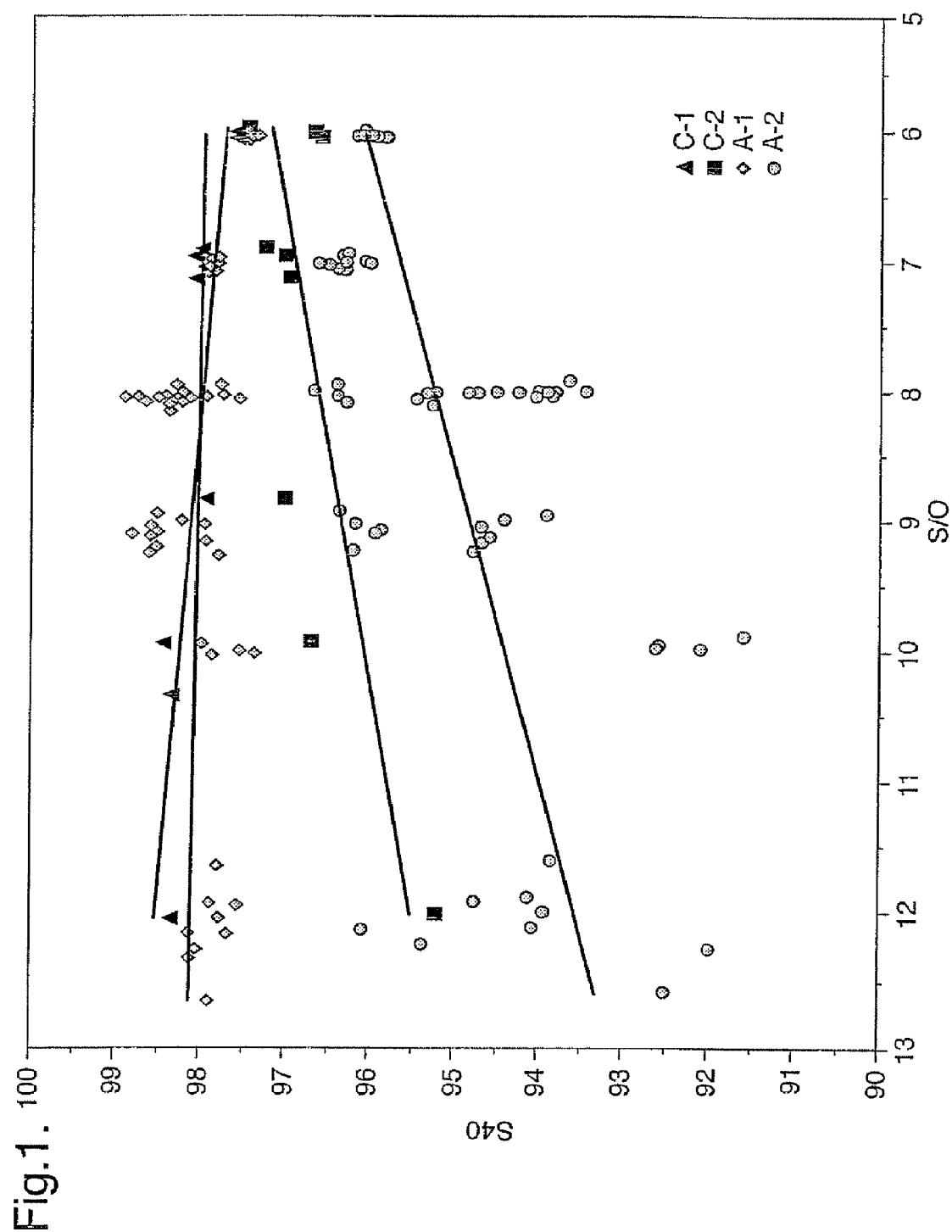
FIGS. 1 and 2 show normalized values of the selectivity and the temperature at a 40% conversion level ("S40" and "T40", respectively), plotted as function of the molar ratio of steam to ethylbenzene ("S/O"), found in a large number of experiments which involve testing of Catalyst A in two reactors in series ("A-1" and "A-2") and testing of Catalyst C in two reactors in series ("C-1" and "C-2"), as described in Example 2, hereinafter.

As used herein, unless defined otherwise, the quantity of metal components in the dehydrogenation catalysts and precursor mixtures, other than the iron components, is expressed as the number of moles of the metal relative to the total number of moles of iron oxide present in the dehydrogenation catalyst, calculated as $Fe_2O_3$.

The dehydrogenation catalysts may independently be based upon iron oxide, cf. for example U.S. Pat. No. 5,689,023, U.S. Pat. No. 5,171,914, U.S. Pat. No. 5,190,906, U.S. Pat. No. 6,191,065, and EP-A-1027928, which are incorporated herein by reference.

Typically, the dehydrogenation catalysts may comprise any iron oxide compound, for example yellow, black and red iron oxides. Preferably, this includes an iron oxide-providing compound selected from goethite, hematite, magnetite, maghemite, lepidocricite and mixtures thereof.

In an embodiment amongst others, the dehydrogenation catalysts may be based upon iron oxide which is obtained by heat decomposition of an iron halide, optionally applying an oxidising atmosphere wherein iron(II) is oxidised to iron(III). The halide may comprise a chloride and/or a bromide. Typically, the iron halide comprises iron dichloride, in particular iron trichloride. Heat decomposition may comprise spray roasting wherein an iron halide solution is sprayed from nozzles into a directly heated reaction chamber, as disclosed in U.S. Pat. No. 5,911,967, which is herein incorporated by reference. Alternative heat decomposition methods utilise the iron halide as a gas or as a solid. The iron oxide which is obtained by heat decomposition of an iron halide may be applied in a quantity of up to 95% w, or even up to 100% w, calculated as $Fe_2O_3$ relative to the total weight of iron oxide, as $Fe_2O_3$, present in the dehydrogenation catalyst. Typically, this quantity is at least 50% w, particular at least 70% w, calculated as $Fe_2O_3$ relative to the total weight of iron oxide, as $Fe_2O_3$, present in the dehydrogenation catalyst.

In an embodiment amongst others, the dehydrogenation catalysts may be based upon iron oxide derived from scrap iron via dehydration of a yellow iron oxide intermediate, frequently depicted as $\alpha$-FeOOH or $Fe_2O_3.H_2O$. This method is known as the Penniman method as it is expressed in U.S. Pat. No. 1,368,748, which is incorporated herein by reference. In embodiments, in particular when the yellow iron oxide is combined with iron oxide which is obtained by heat decomposition of an iron halide, the yellow iron oxide may be applied in a quantity of up to 50% w, calculated as $Fe_2O_3$ relative to the total weight of iron oxide, as $Fe_2O_3$, present in the dehydrogenation catalyst. Preferably, the yellow iron oxide is applied in a quantity of at least 1% w, in particular from 5 to 30% w, on the same basis, for example, 10% w, 15% w, 17% w or 20% w. In other embodiments, the yellow iron oxide may be applied in a quantity of at least 90% w, or at least 95% w, for example up to 100% w, calculated as $Fe_2O_3$ relative to the total weight of iron oxide, as $Fe_2O_3$, present in the dehydrogenation catalyst.

In order to increase the catalyst performance, the dehydrogenation catalysts may, independently, be based on a compound of a lanthanide. The lanthanide is typically a lanthanide of atomic number in the range of from 57 to 62 (inclusive). Preferably the lanthanide is lanthanum or, in particular, cerium. The lanthanide is typically applied in a quantity of at least 0.01 mole, more typically at least 0.03 mole, per mole iron oxide. The lanthanide is typically applied in a quantity of at most 0.5 mole, more typically at most 0.3 mole, most typically at most 0.2 mole, per mole iron oxide. For example, the lanthanide may be applied in a quantity of 0.034 mole, or 0.066 mole, or 0.113 mole, or 0.122 mole, or 0.15 mole, per mole iron oxide.

Typically, one or more compounds of molybdenum, tungsten, copper and/or chromium may be present in one or more of the dehydrogenation catalysts, as an additional component. Compounds of these metals tend to increase the dehydrogenation activity of the catalysts. In preferred embodiments tungsten or, in particular, molybdenum may be applied. Molybdenum, tungsten and chromium may together be applied typically in a quantity of at least 0.001 mole, more typically at least 0.005 mole, per mole iron oxide, and typically in a quantity of most 0.1 mole, more typically at most 0.05 mole, per mole iron oxide. For example, tungsten may be applied in a quantity of 0.0075 mole, or 0.0135 mole, or 0.0275 mole, per mole iron oxide; molybdenum may be applied in a quantity of 0.011 mole, or 0.018 mole, per mole iron oxide; chromium may be applied in a quantity of 0.0085 mole, or 0.035 mole, per mole iron oxide; vanadium may be applied in a quantity of 0.01 mole, or 0.043 mole, or 0.045 mole, or 0.046 mole, or 0.047 mole, per mole iron oxide; and copper may be applied in a quantity of 0.006 mole, or 0.081 mole, per mole iron oxide.

Typically, one or more compounds of an alkali metal may be present in one or more of the dehydrogenation catalysts, as an additional component. Compounds of these metals tend to diminish the deposition of coke on the catalyst during the dehydrogenation, and thereby tend to increase the lifetime of the catalyst. In preferred embodiments, the alkali metal is cesium or, in particular, potassium. The alkali metals may be applied typically in a quantity of at least 0.1 mole, more typically at least 0.2 mole, per mole iron oxide, and typically in a quantity of at most 5 mole, more typically at most 1 mole, per mole iron oxide. For example, the alkali metals may be applied in a total quantity of 0.525 mole, or 0.623 mole, or 0.643 mole, or 0.85 mole, per mole iron oxide.

Typically, one or more compounds of an alkaline earth metal may be present in one or more of the dehydrogenation catalysts, as an additional component. Compounds of these metals tend to increase the selectivity of the catalyst, and to decrease the rate of decline of the catalyst activity. In preferred embodiments, the alkaline earth metal is magnesium or, in particular, calcium. The alkaline earth metals may be applied typically in a quantity of at least 0.001 mole, more typically at least 0.005 mole, per mole iron oxide, and typically in a quantity of at most 1 mole, more typically at most 0.2 mole, per mole iron oxide. For example, the alkaline earth metals may be applied in a total quantity of 0.025 mole, or 0.075 mole, or 0.078 mole, or 0.14 mole, per mole of iron oxide.

It is not material to the invention which kind of lanthanide, alkali metal, molybdenum, tungsten, chromium or alkaline earth metal compounds are applied. Suitably, these metal compounds may, independently, be selected from hydroxides; bicarbonates; carbonates; carboxylates, for example formats, acetates, oxalates and citrates; nitrates; oxides; molybdates; tungstates; chromates; and vanadates. Oxygenated compounds like molybdates; tungstates; chromates; and vanadates may be employed as the acid, or as a suitable salt, such as the potassium, calcium, magnesium or any ammonium salt. The carboxylates are typically derived from carboxylic acids having up to 10 carbon atoms, inclusive, more typically from 1 to 6 carbon atoms, inclusive. More in general, after the calcination the metal compounds are typically present in the dehydrogenation catalysts as the corresponding metal oxides and it is therefore preferred that the metal compounds applied are suitable metal oxide precursors.

The methods by which the dehydrogenation catalysts may be prepared are not material to the invention. Typically, the dehydrogenation catalysts may be prepared, independently, by preparing a mixture of sufficient quantities of the iron oxide(s) and any further metal component(s), such as the metal compounds referred to hereinbefore, and calcining the mixture. Sufficient quantities can be calculated from the composition of the catalyst to be prepared. Examples of applicable methods can be found in U.S. Pat. No. 5,689,023, U.S. Pat. No. 5,171,914, U.S. Pat. No. 5,190,906, U.S. Pat. No. 6,191,065, U.S. Pat. No. 5,668,075, and EP-A-1027928, which are herein incorporated by reference.

Before calcination, the mixture may be shaped into pellets of any suitable form, such as tablets, spheres, pills, saddles, trilobes, tetralobes, rings, stars, and hollow and solid cylinders. The addition of a suitable quantity of water, for example up to 30% w, typically from 2 to 20% w, calculated on the weight of the mixture, may facilitate the shaping into pellets. Suitable shaping methods are pelletising, extrusion, pressing, spraying and spray drying. If desired, spray drying may be extended to include the calcination.

A shaping aid, or extrusion aid, may be applied, for example a saturated or unsaturated fatty acid (such as palmitic acid, stearic acid or oleic acid) or a salt thereof, a polysaccharide derived acid or a salt thereof, or graphite, starch, or cellulose. Any salt of a fatty acid or polysaccharide derived acid may be applied, for example an ammonium salt or a salt of any metal mentioned hereinbefore. The fatty acid may comprise from 6 to 30 carbon atoms (inclusive), preferably from 10 to 25 carbon atoms (inclusive). When a fatty acid or a polysaccharide derived acid is used, it may combine with a metal salt applied in preparing the catalyst, to form a salt of the fatty acid or polysaccharide derived acid. A suitable quantity of the shaping or extrusion aid is, for example, up to 1% w, in particular 0.001 to 0.5% w, relative to the weight of the mixture to be shaped.

The calcination comprises heating the mixture, typically in an inert or oxidising atmosphere, for example in nitrogen, helium, or an oxygen containing gas, such as air, oxygen enriched air or an oxygen/inert gas mixture. The calcination temperature is typically selected in the range of from 600 to 1400° C., preferably in the range of from 800 to 1200° C. For example, the calcination may be carried out at 725° C., or 767° C., or 825° C., or 860° C., or 921° C., or 925° C., or 950° C., or 1040° C. Typically the duration of calcination is from 5 minutes to 12 hours, more typically from 10 minutes to 6 hours, for example 15 minutes, or 1.5 hours, or 3 hours, or 5 hours.

The surface structure of the dehydrogenation catalysts, typically in terms of pore volume, median pore diameter and surface area, is not material to this invention. The skilled person is aware that he can influence the pore volume and the median pore diameter by the selection of the temperature and time of calcination, by the application of pore formers and by the application of a shaping aid or extrusion aid.

Suitably, the pore volume is at least 0.01 ml/g, more suitably at least 0.05 ml/g. Suitably, the pore volume is at most 0.5, preferably less than 0.2, in particular at most 0.18 ml/g, more in particular at most 0.16 ml/g. For example, the pore volume may be 0.094 ml/g, or 0.118 ml/g, or 0.143 ml/g, or 0.161 ml/g. Suitably, the median pore diameter is at least 500 Å, in particular at least 1000 Å. Suitably, the median pore diameter is at most 5000 Å, in particular at most 4500 Å. For example, the median pore diameter may be 1360 Å, or 2080 Å, or 2670 Å, or 3390 Å, or 4320 Å. As used herein, the pore volumes and median pore diameters are as measured by mercury intrusion according to ASTM D4282-92, to an absolute pressure of 6000 psia ($4.2 \times 10^7$ Pa using a Micromeretics Autopore 9420 model (1300 contact angle, mercury with a surface tension of 0.473 N/m). As used herein, median pore diameter is defined as the pore diameter at which 50% of the mercury intrusion volume is reached.

The surface area of the dehydrogenation catalysts is suitably in the range of from 0.01 to 20 $m^2/g$, more suitably from 0.1 to 10 $m^2/g$, for example 2.6 $m^2/g$, or 3.4 $m^2/g$, or 4.9 $m^2/g$, or 5 $m^2/g$. As used herein, surface area is understood to refer to the surface area as determined by the BET (Brunauer, Emmett and Teller) method as described in Journal of the American Chemical Society 60 (1938) pp. 309-316.

As used in this invention, the first dehydrogenation catalyst and the second dehydrogenation catalyst are characterized by their temperature parameters $T_1$ and $T_2$, and selectivity parameter $S_1$ and $S_2$, relative to each other, such that $T_1<T_2$ and $S_1<S_2$.

In preferred embodiments, $T_2-T_1$ is greater than 1° C., in particular $T_2-T_1$ is greater than 2° C., more in particular $T_2-T_1$ is greater than 3° C. When practicing this invention, $T_2-T_1$ will frequently be less than 50° C., more frequently $T_2-T_1$ will be less than 30° C.

In preferred embodiments, $S_2-S_1$ is greater than 0.1% mole, in particular $S_2-S_1$ is greater than 0.2% mole. When practicing this invention, $S_2-S_1$ will frequently be less than 10% mole, more frequently $S_2-S_1$ will be less than 5% mole.

In particular in relation to the dehydrogenation of alkyl aromatic compounds, dehydrogenation catalysts are typically selected such that their temperature parameters, for example $T_1$ and $T_2$, are in the range of from 550 to 650° C., more typically within the range of from 570 to 620° C.

In particular in relation to the dehydrogenation of alkyl aromatic compounds, dehydrogenation catalysts are typically selected such that their selectivity parameters, for example $S_1$ and $S_2$, are in the range of from 85 to 99% mole, more typically within the range of from 90 to 98% mole.

As used herein, numerical values which may be assigned to temperature parameters, for example $T_1$ and $T_2$, and selectivity parameters, for example $S_1$ and $S_2$, are deemed to have been measured in the dehydrogenation of ethylbenzene as the first unsaturated hydrocarbon to obtain styrene as the second unsaturated hydrocarbon applying a tubular reactor which is equipped with heating facilities enabling the reactor to operate under isothermal conditions, as opposed to under adiabatic conditions. The tubular reactor contains a packed bed of the relevant dehydrogenation catalyst and is operated with axial flow under the following isothermal testing conditions: absolute pressure 76 kPa, steam to ethylbenzene molar ratio 10, and LHSV 0.65 l/l.h, wherein initially the temperature of the catalyst bed is kept at 600° C. until stable operation is reached, i.e. typically after at least 400 hours, and subsequently the temperature is adjusted such as to achieve a conversion of 70% mole.

The skilled person will be able to select suitable dehydrogenation catalysts for use in this invention. He may make use of temperature parameters and selectivity parameters of dehydrogenation catalysts as available in the published literature and from catalyst suppliers, or he may apply routine testing of readily available dehydrogenation catalysts.

The dehydrogenation catalysts may differ from each other in one or more compositional aspects, for example in the source, selection and quantity of the components of the catalysts. The dehydrogenation catalysts may also differ in their surface structure, for example in one or more of their surface area, pore size and pore volume.

Suitably the median pore diameter of the second dehydrogenation catalyst is greater than the median pore diameter of the first dehydrogenation catalyst. Typically, the median pore diameter of the second dehydrogenation catalyst may be at least 105%, more typically at least 110% of the median pore diameter of first dehydrogenation catalyst. Typically, the median pore diameter of the second dehydrogenation catalyst is at most 500%, more typically at most 250% of the median pore diameter of first dehydrogenation catalyst.

For example, the median pore diameter of the first dehydrogenation catalyst may be in the range of from 2500 to 3200 Å and the median pore diameter of the second dehydrogenation catalyst may be more than 3200 Å, for example up to 4500 Å. In an alternative embodiment, the median pore diameter of the first dehydrogenation catalyst may be less than 2500 Å, for example down to 1500 Å, and the median pore diameter of the second dehydrogenation catalyst may be in the range of from 2500 to 3200 Å.

The present process for catalytic dehydrogenation of an unsaturated hydrocarbon (hereinafter referred to as "the dehydrogenation process") comprises the first step, in which the feed comprising the first unsaturated hydrocarbon is contacted with the first dehydrogenation catalyst, and the second step, in which a dehydrogenation product obtained from the first step is contacted with the second dehydrogenation catalyst.

The dehydrogenation process is frequently a gas phase process, wherein gaseous reactants are contacted with solid dehydrogenation catalysts. The dehydrogenation catalysts are suitably present in the form of a fluidised bed of catalyst particles, or, more suitably, in the form of a packed bed. In one or in each steps, the process may be carried out as a batch process. However, it is more suitable to carry out the dehydrogenation process in each step as a continuous process. The skilled person will appreciate that hydrogen is a further product of the dehydrogenation process, and that the dehydrogenation in question is a non-oxidative dehydrogenation. Examples of applicable methods of contacting the reactants with the dehydrogenation catalysts and other details of the dehydrogenation process can be found in U.S. Pat. Nos. 5,689,023, 5,171,914, 5,190,906, 6,191,065, and EP-A-1027928, which are herein incorporated by reference.

Each of the dehydrogenation catalysts may be present as a catalyst bed residing in one reactor, for example as stacked layers. It is also possible that one dehydrogenation catalyst or each dehydrogenation catalyst is present as catalyst beds in more than one reactor, for example in two or three reactors. In an alternate embodiment, the dehydrogenation catalysts may be present as separate catalyst beds in a single reactor. The flow of reactants through the catalyst beds may, independently, be axial or radial or lateral.

In each catalyst bed the reaction conditions (for example, the temperature, the pressure, the space velocity, and any presence of water or steam) may or may not be different and may or may not be controlled independently from each other.

In an embodiment, the dehydrogenation process comprises three or more steps, wherein in each of the third and any further steps a dehydrogenation product of a preceding step is contacted with a dehydrogenation catalyst of which the temperature parameter and the selectivity parameter are higher than the temperature parameter and the selectivity parameter of the dehydrogenation catalyst applied in the preceding step. Thus, the dehydrogenation process may comprise a third step in which a reaction product of the second step comprising the first unsaturated hydrocarbon and the second unsaturated hydrocarbon is contacted with a third dehydrogenation catalyst having a temperature parameter $T_3$ and a selectivity parameter $S_3$, such that $T_2<T_3$ and $S_2<S_3$. Likewise, the dehydrogenation process may comprise a fourth step in which a reaction product of the third step comprising the first unsaturated hydrocarbon and the second unsaturated hydrocarbon is contacted with a fourth dehydrogenation catalyst having a temperature parameter $T_4$ and a selectivity parameter $S_4$, such that $T_3<T_4$ and $S_3<S_4$. Analogous further steps are conceivable. In a preferred embodiment amongst others, in the first step of a three-steps process a dehydrogenation catalyst may be used which has a median pore diameter of less than 2500 Å, in the second step a dehydrogenation catalyst may be used which has a median pore diameter in the range of from 2500 Å to 3200 Å and in the third step a dehydrogenation catalyst may be used which has a median pore diameter of more than 3200 Å.

Typically, the first unsaturated hydrocarbon may comprise as the unsaturated moiety an olefinically unsaturated group. For example, the first unsaturated hydrocarbon may be a mono-olefin. Alternatively, and in particular, the first unsaturated hydrocarbon may comprise an aromatic group, in which case the unsaturated hydrocarbon is an alkylaromatic compound. The first unsaturated hydrocarbon comprises typically at least 4 carbon atoms. The first unsaturated hydrocarbon comprises typically at most 20 carbon atoms, inclusive.

The alkylaromatic compound is typically an alkyl substituted benzene, although other alkylaromatic compounds may be applied as well, such as an alkyl substituted naphthalene, anthracene or pyridine. The alkyl substituent may have any carbon number of two or more, for example, up to 6, inclusive. Suitable alkyl substituents are propyl ($-CH_2-CH_2-CH_3$), 2-propyl (i.e. 1-methylethyl, $-CH(-CH_3)_2$), butyl ($-CH_2-CH_2-CH_2-CH_3$), 2-methyl-propyl ($-CH_2-CH(-CH_3)_2$), and hexyl ($-CH_2-CH_2-CH_2-CH_2-CH_2-CH_3$), in particular ethyl ($-CH_2-CH_3$). Examples of suitable alkylaromatic compounds are butyl-benzene, hexyl-benzene, (2-methylpropyl)benzene, (1-methylethyl)benzene (i.e. cumene), 1-ethyl-2-methyl-benzene, 1,4-diethylbenzene, in particular ethylbenzene. A mixture of alkylaromatic compounds may be used.

Examples of suitable mono-olefins are butene-1, butene-2, 2-methylbutene-2, hexene-1, dodecene-1, and mixtures of mono-olefins such as oligomers of ethylene and/or propylene, for example hydrocarbon a mixture of dodecene-1, tetradecene-1, hexadecene-1 and octadecene-1. A mixture of mono-olefins may be used.

It is advantageous to apply water, preferably in the form of steam, as an additional component of the feed. The presence of water will decrease the rate of deposition of coke on the catalyst during the dehydrogenation process. Typically the molar ratio of water to the first unsaturated hydrocarbon in the feed is in the range of from 1 to 50, more typically from 3 to 30, for example 5 or 10.

The dehydrogenation process is typically carried out at a temperature in the range of from 500 to 700° C., more typically from 550 to 650° C., for example 600° C., or 630° C. In an embodiment, the dehydrogenation may be carried out isothermally in one or more of the steps of the process. In other embodiments, in so far as one or more of the steps of the process are carried out in an adiabatic manner, the temperatures mentioned are inlet temperatures, and in those cases, as the dehydrogenation progresses, the temperature may decrease over the catalyst bed in question typically by up to 150° C., more typically by from 10 to 120° C. The absolute pressure is typically in the range of from 10 to 300 kPa, more typically from 20 to 200 kPa, for example 50 kPa, or 120 kPa.

The steps of the process may or may not be operated under the same conditions. For example, it may be advantageous to apply in the second step a higher temperature (or inlet temperature as the case may be) than in the first step. The temperature of the second step may be higher than that of the first step typically by at least 1° C., more typically by 2 to 50° C., in particular by 3 to 30° C. Similar differences may be employed in subsequent steps, if any. As a further example, it may be advantageous to apply in the second step a higher molar ratio of water to the first unsaturated hydrocarbon. The molar ratio of water to the first unsaturated hydrocarbon ratio in the second step may be up to 2 times, more typically up to 1.5 times the molar ratio of water to the first unsaturated hydrocarbon ratio in the first step. This embodiment may be advantageous when the water is applied in the form of hot steam, as to provide heat to the second step. The same applies in an analogous manner to subsequent steps, if any.

When operating the dehydrogenation process as a gas phase process using a packed bed reactor, the LHSV may preferably be in the range of from 0.01 to 10 l/(l.h), more preferably in the range of from 0.1 to 2 l/(l.h). The term "LHSV" stands for the Liquid Hourly Space Velocity, which is the liquid volumetric flow rate of the hydrocarbon feed, measured at normal conditions (i.e. 0° C. and 1 bar absolute), divided by the total volume of the catalyst beds. Typically, the catalyst beds are equal in volumes, but that is not necessarily the case. The volume of the largest catalyst bed may be up to 10 times the volume of the smallest catalyst bed, in particular up to 5 times. In preferred embodiments amongst others, the catalyst bed of the second step is larger than the catalyst bed of the first step. The same applies in an analogous manner to subsequent steps, if any.

In preferred embodiments the dehydrogenation process is operated such that the total conversion of the first unsaturated hydrocarbon is in the range of from 30 to 80% mole, more preferably in the range of from 35 to 75% mole, for example about 67% mole. The conversion which may be reached in each of the separate dehydrogenation steps depends in general on the number of such separate steps in the process. When the dehydrogenation process comprises no more than two separate dehydrogenation steps, the conversion levels in the first step and in the second step may independently be in the range of from 20 to 50% mole, more typically from 25 to 45% mole, for example about 35% mole or about 40% mole. When the dehydrogenation process comprises no more than three separate dehydrogenation steps, the conversion levels in the first step, in the second step and in the third step may independently be in the range of from 10 to 40% mole, more typically from 15 to 35% mole, for example about 25% mole or about 30% mole. When the dehydrogenation process comprises no more than four separate dehydrogenation steps, the conversion levels in the first step, in the second step, in the third step and in the fourth step may independently be in the range of from 5 to 35% mole, more typically from 10 to 30% mole, for example about 15% mole or about 20% mole.

The present dehydrogenation process is in general highly endothermic and would therefore need heat input typically at any dehydrogenation step. Heat may be provided by any conventional method, such as by using a furnace equipped with conventional burners, or by combining the feed comprising the first unsaturated hydrocarbon with steam.

A relatively high heat input may be needed in the second dehydrogenation step because in the first step a dehydrogenation catalyst is used which has a relatively high activity so that the conversion level in the first step may be relatively high leading to a relatively low temperature of the reaction product of the first step if operated in adiabatic mode. Alternatively, or in addition, such relatively high heat input may be needed because in the second dehydrogenation step a dehydrogenation catalyst is used which has a relatively low activity so that the second step may be operated at a relatively high temperature. Such relatively high heat input may advantageously be provided by flame-less combustion of a hydrocarbon. Thus, in a preferred embodiment, amongst others, the manufacturing plant of this invention comprises an apparatus for the flame-less combustion of a hydrocarbon configured to heat the reaction product formed in the first catalyst bed. A suitable apparatus for flame-less combustion of a hydrocarbon and methods of using the apparatus are known in the art, for example from WO-99/18392 and U.S. Pat. No. 5,255,742, which are incorporated herein by reference.

The second unsaturated hydrocarbon may be recovered from the dehydrogenation product by any known means. For example, the process of this invention may include a fractional distillation or reactive distillation. The dehydrogenation process may include a hydrogenation step in which at least a portion of a product which has a higher degree of unsaturation than the second unsaturated hydrocarbon is removed by hydrogenation to yield a further portion of the second unsaturated hydrocarbon. In particular, the process for the dehydrogenation of an alkylaromatic compound may include a hydrogenation step in which at least a portion of the product is subjected to hydrogenation by which at least a portion of the alkynylaromatic compound, if any is present, is converted into the alkenylaromatic compound. The portion of the product subjected to hydrogenation may be a portion of the product which is enriched in the product which has a higher degree of unsaturation than the second unsaturated hydrocarbon. Such hydrogenation is known in the art. For example, the methods known from U.S. Pat. No. 5,504,268, 5,156,816 and 4,822,936, which are incorporated herein by reference, are readily applicable to the present invention.

The second unsaturated hydrocarbon is a useful product for application in a wide variety of processes, such as in polymerization processes and copolymerisation processes. For example, styrene obtained may be used in the production of polystyrene, and conjugated di-olefins may be used in the production of rubbers and the like. The present invention leads to a more attractive process for the production of the second unsaturated hydrocarbon and concurrently to a more attractive process which comprises producing the second unsaturated hydrocarbon and the subsequent use of the obtained second unsaturated hydrocarbon in the manufacture of polymers and copolymers which comprise monomer units of the second unsaturated hydrocarbon. For applicable polymerization catalysts, polymerization processes, polymer processing methods and uses of the resulting polymers, reference is made to H F Marks, et al. (Ed.), "Encyclopedia of Polymer Science and Engineering", $2^{nd}$ Edition, New York, Volume 16, pp. 1-246, and the references cited therein, which is/are incorporated herein by reference.

The invention will be illustrated by means of the following, non-limiting examples.

EXAMPLE 1

A dehydrogenation catalyst, Catalyst A, was prepared as follows. A paste was made by mixing the following ingredients: iron oxide (Hoogovens Regenerated iron oxide, type RIO-250), yellow iron oxide (Bayer, type 920Z), cerium carbonate, molybdenum trioxide, calcium carbonate, and water (about 10%, relative to the weight of the dry mixture). The paste was extruded to form 3-mm diameter cylinders cut into 6-mm lengths. The pellets were dried in air at 170° C. for 2 hours and subsequently calcined in air at 845° C. for 1 hour. After calcination the composition of Catalyst A was 0.623 mole potassium, 0.122 mole cerium, 0.0178 mole molybdenum, 0.025 mole calcium, all per mole of iron oxide, as $Fe_2O_3$, present. The quantity of yellow iron oxide was 10%, as $Fe_2O_3$, relative to the total quantity (number of moles) of iron oxide, as $Fe_2O_3$, present in the catalyst. Catalyst A had a median pore diameter of 1900 Å.

For Catalyst A it was found that the temperature parameter was 584° C. and that the selectivity parameter was 95.0% mole.

A dehydrogenation catalyst, Catalyst B, was made in a manner similar to the preparation of Catalyst A, except that the iron oxide applied was exclusively made by the Penniman process, and the calcination was carried out at 830° C., for 1 hour, instead of 845° C., for 1 hour. The composition of Catalyst B was 0.548 mole potassium, 0.088 mole cerium, 0.011 mole molybdenum, 0.067 mole calcium, all per mole of iron oxide, as $Fe_2O_3$, present. Catalyst B had a median pore diameter of 2300 Å. The temperature parameter of Catalyst B was 591° C.; the selectivity parameter was 94.7% mole.

A dehydrogenation catalyst, Catalyst C, was made in a manner similar to the preparation of Catalyst A, except that that the calcination was carried out at 965° C., for 1 hour, instead of 845° C., for 1 hour. The composition of Catalyst C was 0.518 mole potassium, 0.066 mole cerium, 0.022 mole molybdenum, 0.027 mole calcium, all per mole of iron oxide, as $Fe_2O_3$, present. Catalyst C had a median pore diameter of 3300 Å. The temperature parameter of Catalyst C was 596° C.; the selectivity parameter was 95.8% mole.

A dehydrogenation catalyst, Catalyst D, was prepared as follows. A mixture was made by mixing iron oxide (Hoogovens Regenerated iron oxide, type RIO-250) and molybdenum trioxide. The mixture was calcined in air at 825° C. for 1 hour. The calcined powder was then mixed with cerium carbonate, calcium carbonate, and water (about 10%, relative to the weight of the dry mixture), to form a paste. The paste was extruded to form 3-mm diameter cylinders cut into 6-mm lengths. The pellets were dried in air at 170° C. for 2 hours and subsequently calcined in air at 790° C., for 1 hour. The composition of Catalyst D was 0.612 mole potassium, 0.096 mole cerium, 0.040 mole molybdenum, 0.025 mole calcium, all per mole of iron oxide, as $Fe_2O_3$, present. Catalyst D had a median pore diameter of 4000 Å. The temperature parameter of Catalyst D was 601° C.; the selectivity parameter was 95.8% mole.

EXAMPLE 2 (PROPHETIC)

In four experiments, Experiments I-IV, samples of Catalysts A and C of Example 1 are used in the preparation of styrene from ethylbenzene in two steps, viz. under adiabatic conditions in two reactors in series designed for continuous operation. In the two reactors the catalyst beds have the same dimensions. The reaction conditions in each reactor (step) are as follows: Catalyst A or C, as indicated in Table I; inlet temperature: as indicated in Table I; average absolute pressure 64 kPa, steam to ethylbenzene molar ratio 10, LHSV 0.42 l/l.h. The conditions are selected such as to provide in each reactor (step) a conversion of 40% mole of ethylbenzene, providing a total conversion of 64% mole.

Figure 2:
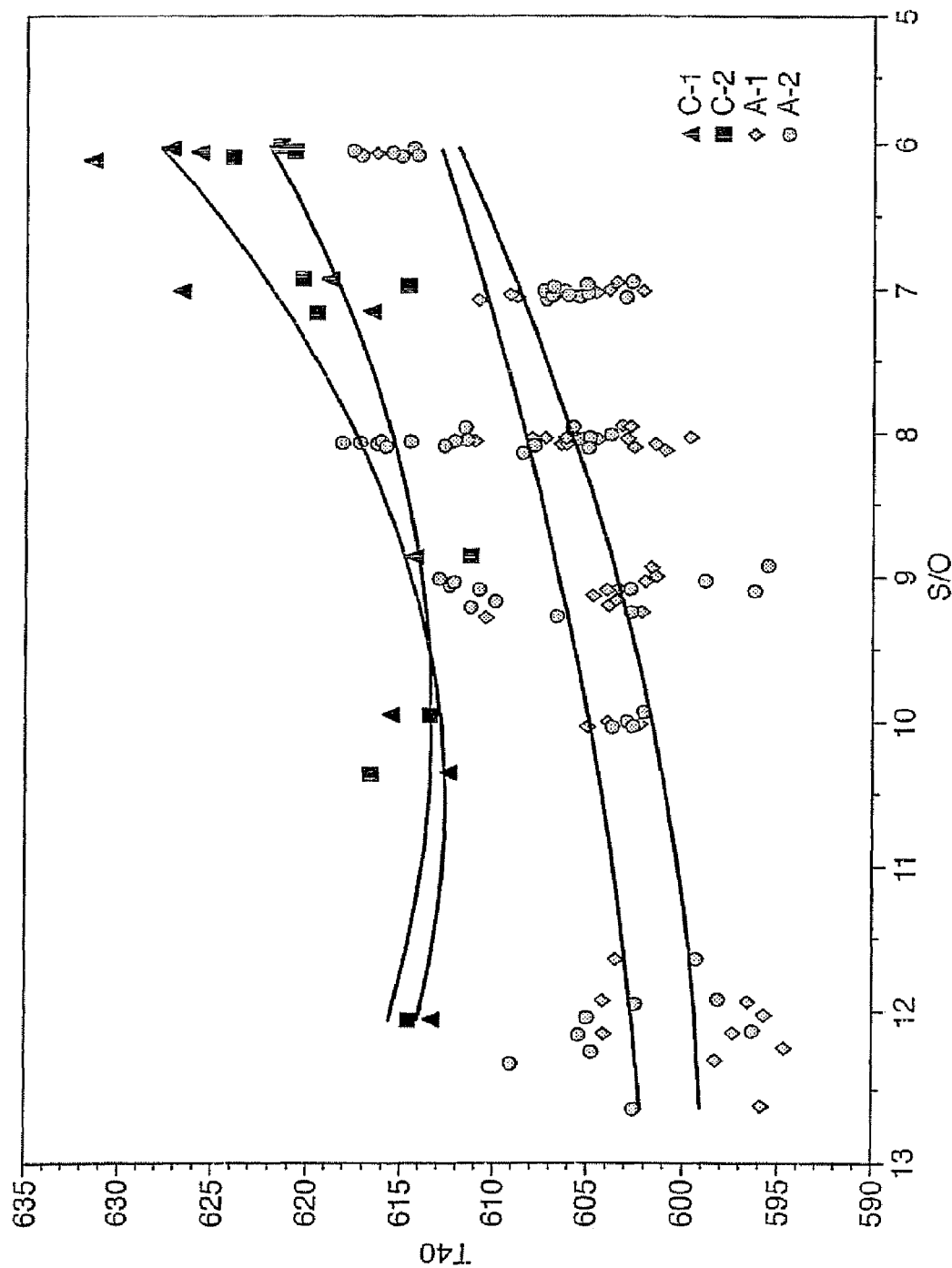

The results are depicted in Table I. The values recorded in Table I for the selectivity and inlet temperature of the first and the second step result from a large number of experiments relating to the preparation of styrene from ethylbenzene, as follows. The experiments involve testing of Catalyst A in two reactors in series and testing of Catalyst C in two reactors in series, and they cover continuous operation of both reactors under adiabatic conditions in an average pressure range of from 40 to 120 kPa absolute, an S/O range from 5.9 to 12.7, and an LHSV range of from 0.30 to 0.58 l/l.h. The selectivity and the temperature found at the 40% conversion levels for each reactor (step) have been normalised to the reaction conditions as specified in the previous paragraph, by applying to the experimental selectivity and temperature values linear factors which adjust for differences in average pressure, S/O, LHSV and catalyst age. FIGS. 1 and 2 show the resulting normalized values of the selectivity and the temperature at a 40% conversion level ("S40" and "T40", respectively), plotted as function of the experimental values of the steam to ethylbenzene molar ratio ("S/O"). "A-1" and "A-2" represent the results of Catalyst A in the first reactor (step) and in the second reactor (step), respectively. "C-1" and "C-2" represent the results of Catalyst C in the first reactor (step) and in the second reactor (step), respectively. FIGS. 1 and 2 also show the trend lines for S40 vs. S/O and T40 vs. S/O which have been found by least squares linear regression and least squares quadratic regression, respectively. The values of S40 and T40 read from the trend lines at S/O 10 are the values recorded in Table I for the selectivity and inlet temperature of the first and the second step. These are considered to be representative values of the selectivity and the temperature at the 40% conversion levels when the catalysts are employed in a commercial unit operated at the reaction conditions as specified in the previous paragraph.

TABLE I

| | Experiment | | | |
|---|---|---|---|---|
| | I *) | II *) | III **) | IV *) |
| First step | Catalyst A | Catalyst C | Catalyst A | Catalyst C |
| Conversion, % mole | 40 | 40 | 40 | 40 |
| Selectivity, % mole | 98.05 | 98.26 | 98.05 | 98.26 |
| Inlet temperature, °C. | 601.1 | 612.4 | 601.1 | 612.4 |
| Second step | Catalyst A | Catalyst C | Catalyst C | Catalyst A |
| Conversion, % mole | 40 | 40 | 40 | 40 |
| Selectivity, % mole | 93.99 | 95.83 | 95.83 | 93.99 |
| Inlet temperature, °C. | 604.4 | 612.9 | 612.9 | 604.4 |
| Overall | | | | |
| Conversion, % mole | 64 | 64 | 64 | 64 |
| Selectivity, % mole | 96.53 | 97.35 | 97.22 | 96.66 |
| Average inlet temperature, °C. | 602.8 | 612.6 | 607.0 | 608.4 |

*) For comparison, not according to the invention
**) According to the invention On the basis of a linear interpolation between Experiments I and II, it can be calculated that for an average inlet temperature of 607.0° C. the overall selectivity would amount to 96.88% mole, and that for an average inlet temperature of 608.4° C. the overall selectivity would amount to 96.99% mole. In experiment III, at an average inlet temperature of 607.0° C., the overall selectivity is 97.22% mole, which is 0.34% mole higher than the calculated value. For comparison, in Experiment IV, at an average inlet temperature of 608.4° C., the overall selectivity is 96.66% mole, which is 0.33% mole lower than the calculated value. Thus, in accordance with this invention, by employing a configuration of catalysts as in Experiment III the overall selectivity will be higher after eliminating the influence of different average inlet temperatures, when compared with employing a single type of catalyst, as in Experiments I and II, and in particular when compared with employing a configuration of catalysts as disclosed in U.S. Pat. No. 3,223,743, as in Experiment IV.

Without wishing to be bound by theory it is believed that the invention benefits from the combination of (1) employing at a relatively low overall conversion level a high activity catalyst providing a relatively high rate/low operating temperature, without substantially compromising the selectivity, and (2) employing at a relatively high overall conversion level a high selectivity catalyst providing at that conversion level a substantially higher selectivity advantage over the high activity catalyst than when compared at the relatively low overall conversion level.

An Experiment V may be carried out which is similar to Experiment III, except that Catalyst A is replaced by Catalyst B of Example 1.

An Experiment V may be carried out which is similar to Experiment III, except that Catalyst C is replaced by Catalyst D of Example 1.

What is claimed is:

1. A manufacturing plant for carrying out a process for the catalytic dehydrogenation of a first unsaturated hydrocarbon to form a second unsaturated hydrocarbon which has one olefinically unsaturated bond more than the first unsaturated hydrocarbon and otherwise an unchanged carbon skeleton, which plant comprises: a first catalyst bed which is configured to receive a feed comprising the first unsaturated hydrocarbon, and which first catalyst bed comprises a first dehydrogenation catalyst having a temperature parameter $T_1$, and a selectivity parameter $S_1$, and a second catalyst bed which is configured to receive a reaction product formed in the first catalyst bed comprising the first unsaturated hydrocarbon and the second unsaturated hydrocarbon, and which second catalyst bed comprises a second dehydrogenation catalyst having a temperature parameter $T_2$ and a selectivity parameter $S_2$, such that $T_1 < T_2$ and $S_1 < S_2$, wherein "temperature parameter" means the temperature, in ° C., at which the dehydrogenation catalyst in question provides under defined testing conditions a conversion of the first unsaturated hydrocarbon of 70% mole, and "selectivity parameter" means the selectivity, in % mole, to the second unsaturated hydrocarbon which is then achieved.

2. A manufacturing plant as claimed in claim 1, which comprises an apparatus for the flame-less combustion of hydrocarbon configured to heat the reaction product formed in the first catalyst bed.

3. A manufacturing plant as claimed in claim 1, wherein $T_2 - T_1$, is in the range of from 1 to 50° C.

4. A manufacturing plant as claimed in claim 1, wherein $S_2 - S_1$ is in the range of from 0.1 to 5% mole.

5. A manufacturing plant as claimed in claim 1, wherein the dehydrogenation catalysts are selected such that their temperature parameters are in the range of from 550 to 650° C., wherein the temperature parameters are as measured in the dehydrogenation of ethylbenzene to obtain styrene applying a tubular reactor which contains a packed bed of the relevant dehydrogenation catalyst and which is operated with axial flow under the following isothermal testing conditions: absolute pressure 76 kPa, steam to ethylbenzene molar ratio 10, and LHSV 0.65 l/l.h, wherein initially the temperature is kept at 600° until stable operation is reached, and subsequently the temperature is adjusted such as to achieve a conversion of 70% mole.

6. A manufacturing plant as claimed in claim 1, wherein the dehydrogenation catalysts are selected such that their selectivity parameters are in the range of from 90 to 99% mole, wherein the selectivity parameters are as measured in the dehydrogenation of ethylbenzene to obtain styrene applying a tubular reactor which contains a packed bed of the relevant dehydrogenation catalyst and which is operated with axial flow under the following isothermal testing conditions: absolute pressure 76 kPa, steam to ethylbenzene molar ratio 10, and LHSV 0.65 l/l.h, wherein initially the temperature is kept at 600° C. until stable operation is reached, and subsequently the temperature is adjusted such as to achieve a conversion of 70% mole.

7. A manufacturing plant as claimed in claim 1, wherein the dehydrogenation catalysts are based upon iron oxide.

8. A manufacturing plant as claimed in claim 6, wherein the dehydrogenation catalysts, independently, are based in addition upon one or more compounds selected from one or more compounds of a lanthanide, one or more compounds of molybdenum, tungsten, copper or chromium, one or more compounds of an alkali metal, and one or more compounds of an alkaline earth metal.

9. A manufacturing plant as claimed in claim 7, wherein the dehydrogenation catalysts, independently, are based in addition upon one or more compounds selected from one or more compounds of cerium, one or more compounds of molybdenum or tungsten, one or more compounds of potassium, and one or more compounds of calcium or magnesium.

10. A manufacturing plant as claimed in claim 1 further comprising a reaction apparatus for polymerizing the second unsaturated hydrocarbon to form a polymer or copolymer comprising monomer units derived from the second unsaturated hydrocarbon.

* * * * *